(12) United States Patent
Kubischta et al.

(10) Patent No.: US 11,243,417 B2
(45) Date of Patent: Feb. 8, 2022

(54) PERSONAL PROTECTIVE EQUIPMENT (PPE) FOR COVERING THE FACE

(71) Applicants: Keith E. Kubischta, Poway, CA (US); Karen M. Kubischta, Poway, CA (US)

(72) Inventors: Keith E. Kubischta, Poway, CA (US); Karen M. Kubischta, Poway, CA (US)

(*) Notice: Subject to any disclaimer, the term of this patent is extended or adjusted under 35 U.S.C. 154(b) by 0 days.

(21) Appl. No.: 17/347,071

(22) Filed: Jun. 14, 2021

(65) Prior Publication Data

US 2022/0007757 A1    Jan. 13, 2022

Related U.S. Application Data

(60) Provisional application No. 63/050,492, filed on Jul. 10, 2020.

(51) Int. Cl.
  *G02C 11/02* (2006.01)
  *G02C 11/00* (2006.01)
  *A61B 90/00* (2016.01)

(52) U.S. Cl.
  CPC .............. *G02C 11/12* (2013.01); *A61B 90/05* (2016.02); *A61B 90/08* (2016.02); *G02C 11/02* (2013.01)

(58) Field of Classification Search
  CPC ......... A60B 90/05; A60B 90/08; G02C 11/12; G02C 11/02
  USPC ........................ 351/47, 51, 52, 123; 2/13, 15
  See application file for complete search history.

(56) References Cited

U.S. PATENT DOCUMENTS

| | | | | |
|---|---|---|---|---|
| 3,594,816 A | * | 7/1971 | Webb | A42B 3/225 2/10 |
| 5,206,956 A | | 5/1993 | Olson | |
| 5,614,963 A | * | 3/1997 | Parker | G02C 7/10 2/13 |
| 5,692,522 A | * | 12/1997 | Landis | A61F 9/02 128/857 |
| 6,007,196 A | * | 12/1999 | Saba | G02C 7/16 2/13 |
| 6,260,964 B1 | * | 7/2001 | Kroman | G02C 9/04 351/47 |
| 6,745,396 B1 | | 6/2004 | Landis et al. | |
| 6,996,846 B1 | * | 2/2006 | Karapetyan | A41D 13/1184 2/10 |
| 8,291,512 B2 | | 10/2012 | Stoll | |
| 2014/0109918 A1 | | 4/2014 | Nabai | |

(Continued)

OTHER PUBLICATIONS

Video: How to clip to glasses; https://www.protexfaceshields.com/products/p/fsx (Year: 2013).*

(Continued)

*Primary Examiner* — Kristina M Deherrera
(74) *Attorney, Agent, or Firm* — Wagenkencht IP Law Group PC

(57) ABSTRACT

An article of personal protective equipment (PPE) for covering a wearer's face when wearing loupes and/or a light mounted to an eyeglass frame, the apparatus including a set of adapters, each adapter mounted or configured for mounting to an eyeglass frame, wherein each adapter has an outward extending protrusion; and a transparent face shield with opposing sidewalls joined by a convex front with upper and lower portions angled inward to cover the wearer's face when wearing the loupes and/or light, each sidewall configured to engage one of the protrusions to align an apex of the convex with the loupes and/or light.

4 Claims, 18 Drawing Sheets

(56) References Cited

U.S. PATENT DOCUMENTS

2016/0353815 A1* 12/2016 Nabai .................... A61F 9/022
2021/0373359 A1* 12/2021 Tsai ...................... G02C 11/12

OTHER PUBLICATIONS

"FSX In Use", Protex Face Shields, Jun. 4, 2020, https://www.protexfaceshields.com/wp-content/uploads/2013/12/FSX-in-use-scaled.jpg.

* cited by examiner

PERSONAL PROTECTIVE EQUIPMENT (PPE) FOR COVERING THE FACE

CROSS REFERENCE TO RELATED APPLICATIONS

This application claims priority to U.S. provisional patent application No. 63/050,492, filed Jul. 10, 2020, the entire content of which is herein incorporated by reference in its entirety.

TECHNICAL FIELD

The invention relates generally to personal protective equipment (PPE) for healthcare professionals, and more specifically to a personal protective face shield for use with loupes and/or lighting mounted to an eyeglass frame.

BACKGROUND OF THE INVENTION

Healthcare professionals, including but not limited to surgeons and other physicians, physician assistants, dentists, and dental hygienists, come in contact with numerous patients within the medical, surgical, veterinary, and dental fields of practice. Due to their need to work directly within the body of numerous patients, it is crucial that these healthcare professionals use appropriate personal protective equipment (PPE). To this end, healthcare professionals are increasingly using face shields.

However, many healthcare professionals require specialized equipment that can make most PPE difficult to use. In particular, healthcare professionals frequently use specialized, handsfree loupes and lighting attached to glasses, whether prescription glasses or safety glasses, which can interfere with conventional face shields.

A loupe is a simple, small magnification device used to see small details more closely. Loupes are often attached to medical safety glasses either through-the-lenses, or in a flip-down mechanism. Healthcare professionals frequently use loupes to see areas of the body under magnification, while maintaining proper body ergonomics. Similarly, a loupes light allows healthcare professionals to focus light on a body part and to provide shadow-free light for the practitioner since it is mounted to the loupes.

Since both loupes and loupes lights tend to extend outward beyond the glasses, wearing a conventional face shield requires extending the face shield far from the face. This creates a large gap at the top and bottom of the face shield, which can reduce the facial coverage above and below the face shield especially when leaning towards the patient.

Accordingly, there remains a need to provide improved personal protective equipment (PPE) to provide better coverage of a wearer's face when wearing loupes and/or light attached to pair of eyeglasses.

BRIEF SUMMARY OF THE INVENTION

The invention addresses the above deficiencies in the state of the art and provides related benefits, in particular, in one aspect of the invention, an article of personal protective equipment (PPE) for providing coverage of a wearer's face when wearing loupes and/or a light mounted to an eyeglass frame is provided, which includes a set of adapters, each adapter mounted or configured for mounting to an eyeglass frame, each adapter having an outward extending protrusion; and a transparent face shield with opposing sidewalls joined by a convex front with upper and lower portions angled inward to cover the wearer's face when wearing the loupes and/or light, each sidewall configured to engage one of the protrusions to align an apex of the convex with the loupes and/or light to substantially cover the face.

Preferably, the protrusion of the adapter includes a bulbous member. The adapter can be integral with the eyeglass frame, attached to the eyeglass frame such as by using a bolting mechanism, clamped to the eyeglass frame, and/or tied to the eyeglass frame. In some embodiments, the adapter includes two wings, optionally attached to one another at one end, for clamping to the frame. In further embodiments, the two wings have through bores on opposing sides of the protrusion and the wings are clamped by strapping the wings together through the through bores.

The sidewall has an engagement mechanism that reversibly engages the protrusion. A preferred engagement mechanism includes a pronged clip extending through the sidewall so that prongs, which are preferably shaped complementary to the protrusion, are actuated from outside of the face shield to selectively grasp and release the protrusion. In some embodiments, the prongs are opened and closed by pinching then releasing a pinchable handle, which is positioned outside of the face shield. In some embodiments, the prongs are elongated to form an adjustable track for adjustably positioning the protrusion towards and away from the convex front of the face shield, which moves the face shield forward and back.

In other embodiments, each sidewall of the face shield includes an aperture sized to accept the protrusion. In still other embodiments, each sidewall has a recess shaped complementary to the protrusion. The recess can have a bendable contour for bending around the protrusion. In some embodiments, engagement between the sidewall and adapter is a friction-fit engagement. In others, the engagement includes a detest mechanism, a spring-loaded mechanism, or a position locking mechanism. In still other embodiments, each sidewall has a track configured to accept the protrusion, thereby permitting the face shield to be adjusted forwards and rearwards by sliding the adapter along the track.

In a related aspect of the invention, another article of personal protective equipment (PPE) for covering a wearer's face is provided, the article having a set of adapters, each adapter having an outward extending protrusion that is mounted or configured for mounting to a temple of an eyeglass frame; and a face shield having pronged clips that extend through the face shield to reversibly grasp the set of adapters and which are actuated outside of the face shield. In some embodiments, the pronged clips each have a pinchable handle that opens a pair of prongs when pinched. In some embodiments, the pronged clips are elongated to form an adjustable track for accepting, releasing, and adjustably positioning the set of adapters towards and away from a front of the face shield. In some embodiments, the face shield has opposing sidewalk joined by a convex front with upper and lower portions angled inward to cover a wearer's face

BRIEF DESCRIPTION OF THE DRAWINGS

Embodiments of the invention can be better understood with reference to the following drawings, which are part of the disclosure and represent preferred embodiments. The components in the drawings are not necessarily to scale, emphasis instead being placed upon illustrating the principles of the invention. And, in the drawings, like reference numerals designate corresponding parts throughout the several views.

DESCRIPTION OF THE INVENTION

Figure 1:
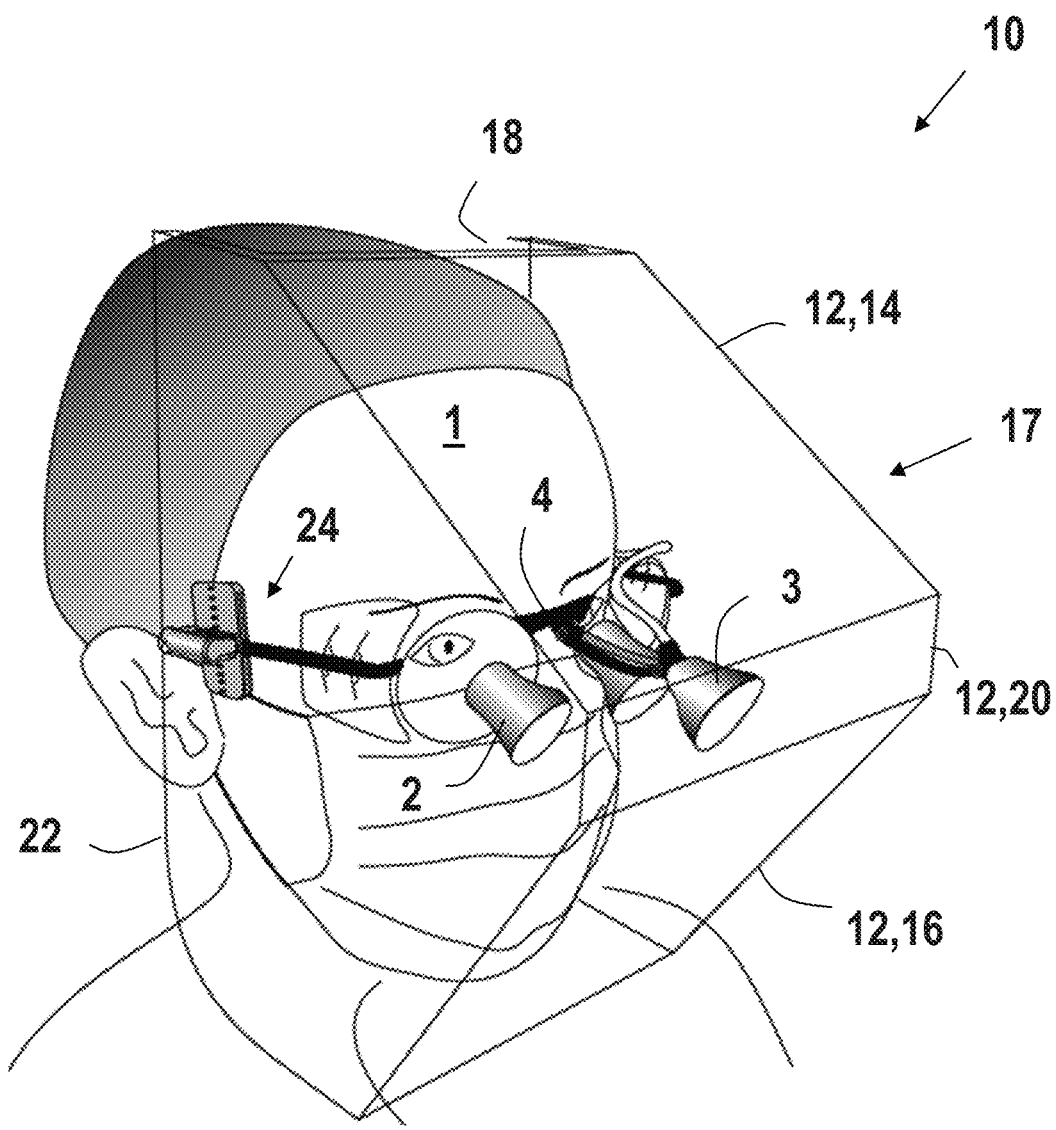
FIG. 1 is a right, top, and front isometric view of an individual wearing an exemplary face shield 12 depicting the alignment of the apex at the middle portion 20 of the convex front 17 with a loupes 2 and a loupes light 3.
Figure 2:
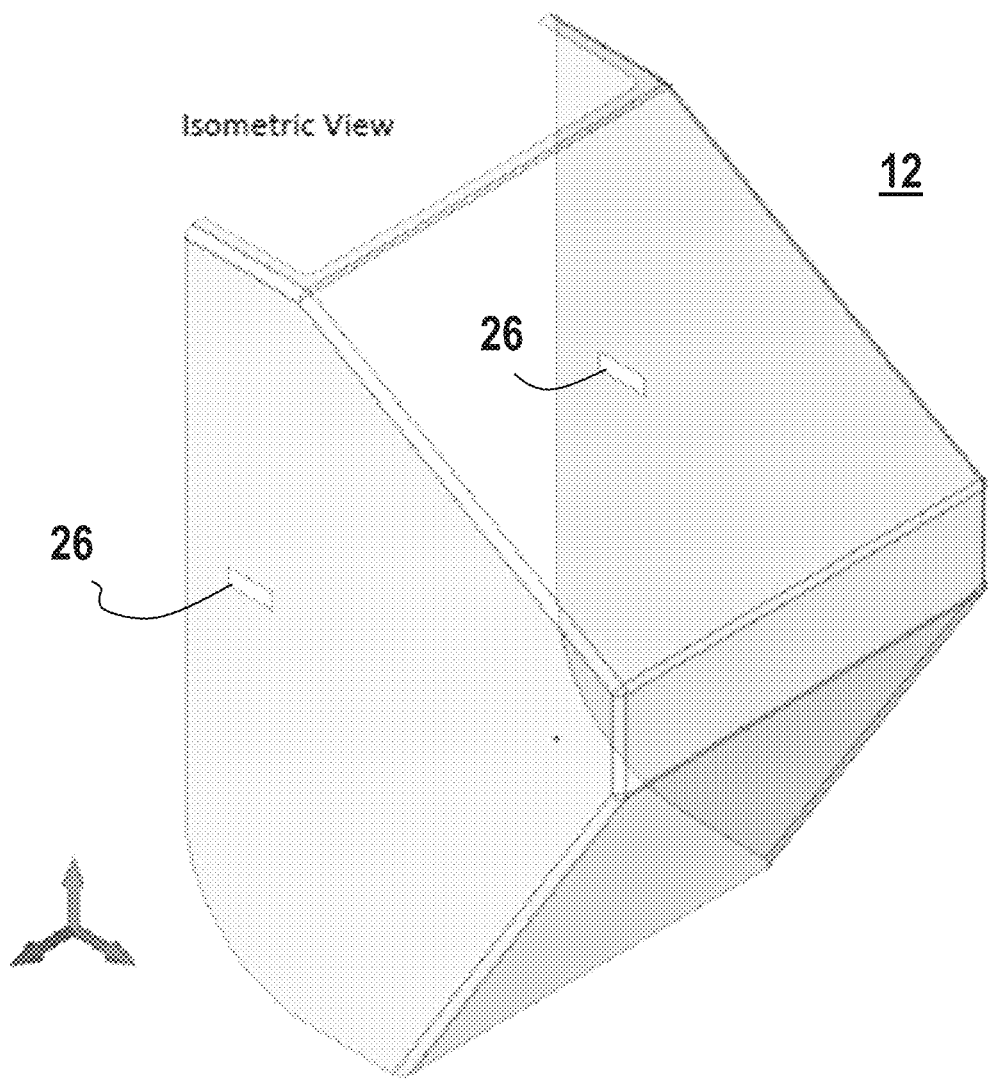
FIG. 2 is a right, top, and front isometric view of the face shield 12 of FIG. 1.

Beginning with FIG. 1, an article of personal protective equipment (PPE) 10 for covering a wearer's face 1 when wearing loupes 2 and/or a light 3 mounted to an eyeglass frame 4 is depicted. This is accomplished at least in part by providing a transparent face shield 12 shaped generally convex so that opposing upper and lower portions 14, 16 of a front portion 17 are angled inward to cover both the top and bottom of the wearer's face 1. At the top is preferably a cutaway 18 for improved fitting around the crown of the wearer's head. The middle portion 20 of the face shield 12, generally characterized as an apex of the generally convex shape, extends outward to provide sufficient space to cover the loupes 2 and/or light 3. Opposing transparent sides 22 preferably extend along the entire height of the face shield 12 to cover the side of the wearer's face 1. Preferably, the sides 22 are configured to at least partially cover the ears. Preferably, the face shield 12 is formed from a bendable, light weight, and transparent polymer such as but not limited to polypropylene. The face shield 12 is worn by engaging the opposing side walls 22 of the face shield 12 with a set of adapters 24, which themselves are mounted or configured for mounting to an eyeglass frame 4, which the individual wears.

Figure 3:
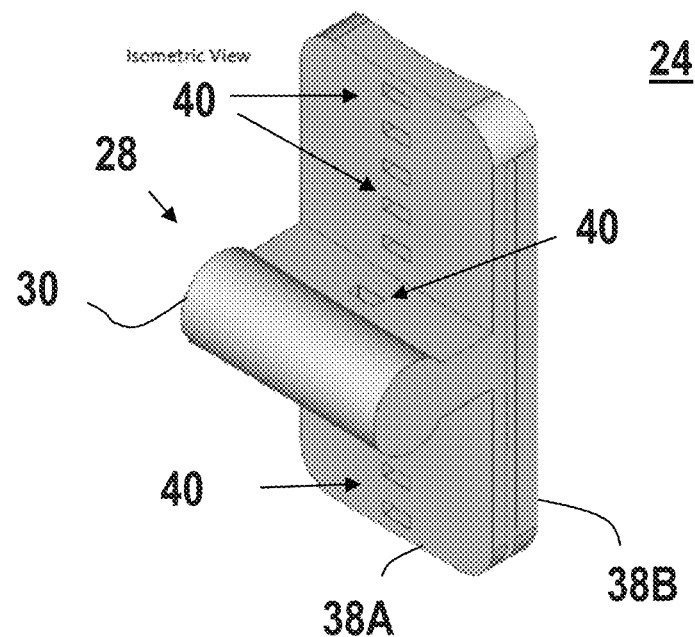
FIG. 3 is a right, top, and front isometric view of an exemplary adapter 24 having two wings 38A, 38B and an outward extending protrusion 28.
Figure 4:
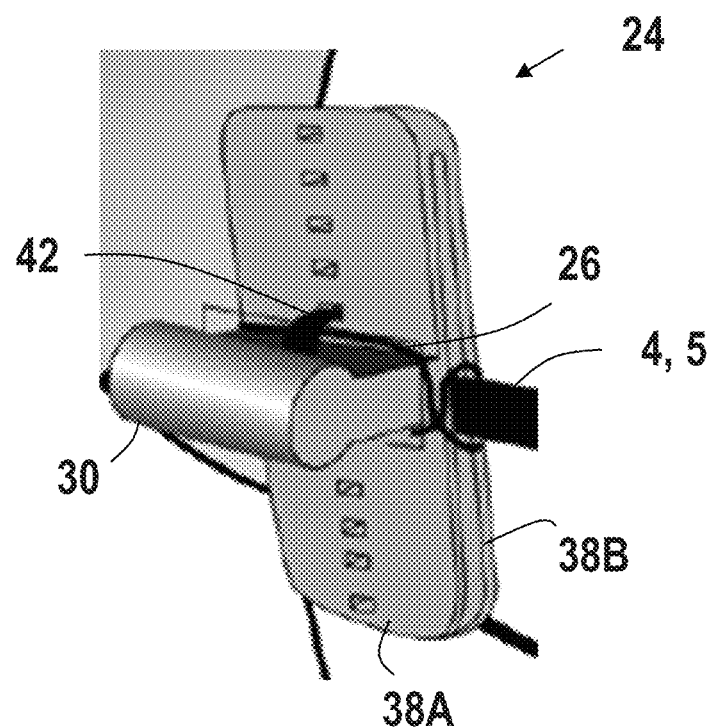
FIG. 4 is a right, top, and front isometric view of the adapter 24 of FIG. 3 shown clamped around the temple 5 and through the aperture 26 of the face shield 12 of FIG. 2.

FIGS. 1-4 depict in more detail how an exemplary face shield 12 is secured. In particular, each sidewall 22 can have an aperture 26 sized for fitting the adapter 24 there through. FIGS. 3-4 depict a preferred adapter 24 including a protrusion 28 configured with a bulbous member 30, Shown more clearly in FIG. 4, the bulbous member 30 is pushed through the aperture 26. Now returning collectively to FIGS. 1-4, it has been found that by sizing the aperture 26 to about the same size as the bulbous member 30, the face shield 12 is easily pressed over the bulbous member 30 to engage the adapter 24. It has also been found that the bulbous member 30 successfully prevents inadvertent release of the sidewall 22 by the adapter 24. In particular, gravitational forces tend to pull the aperture 24 below the bulbous member 30, thereby preventing inadvertent removal.

Figure 5:
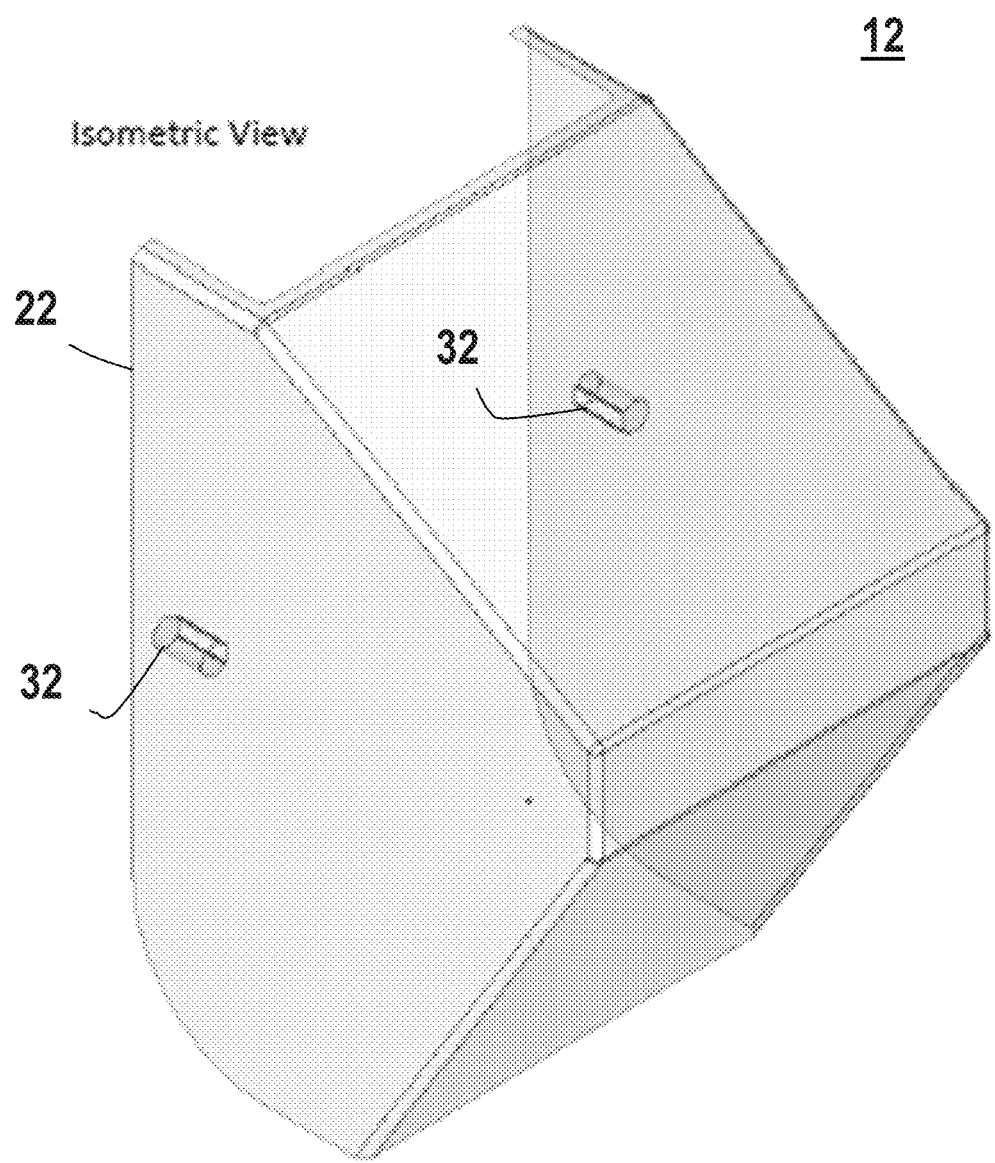
FIG. 5 is a right, top, and front isometric view of another exemplary face shield 12 equipped with a recess 32 for engagement.
Figure 6:
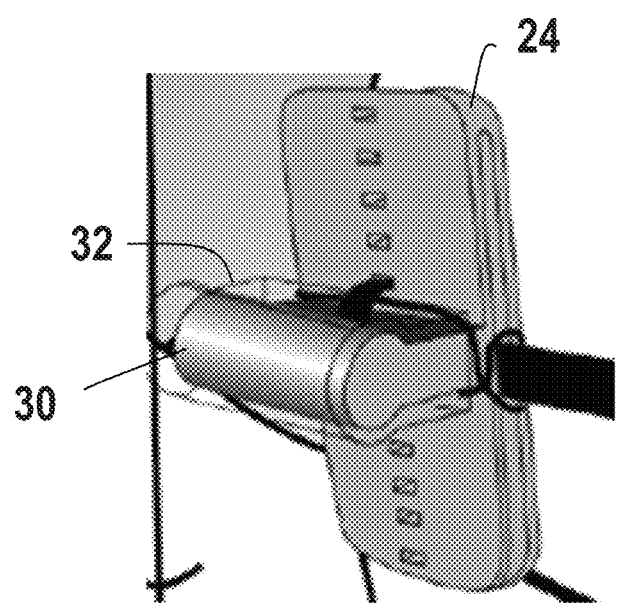
FIG. 6 is a right, top, and front isometric view of the adapter 24 of FIG. 3 shown clamped around the temple 5 and engaged with the recess 32 of the face shield 12 of FIG. 5.
Figure 7:
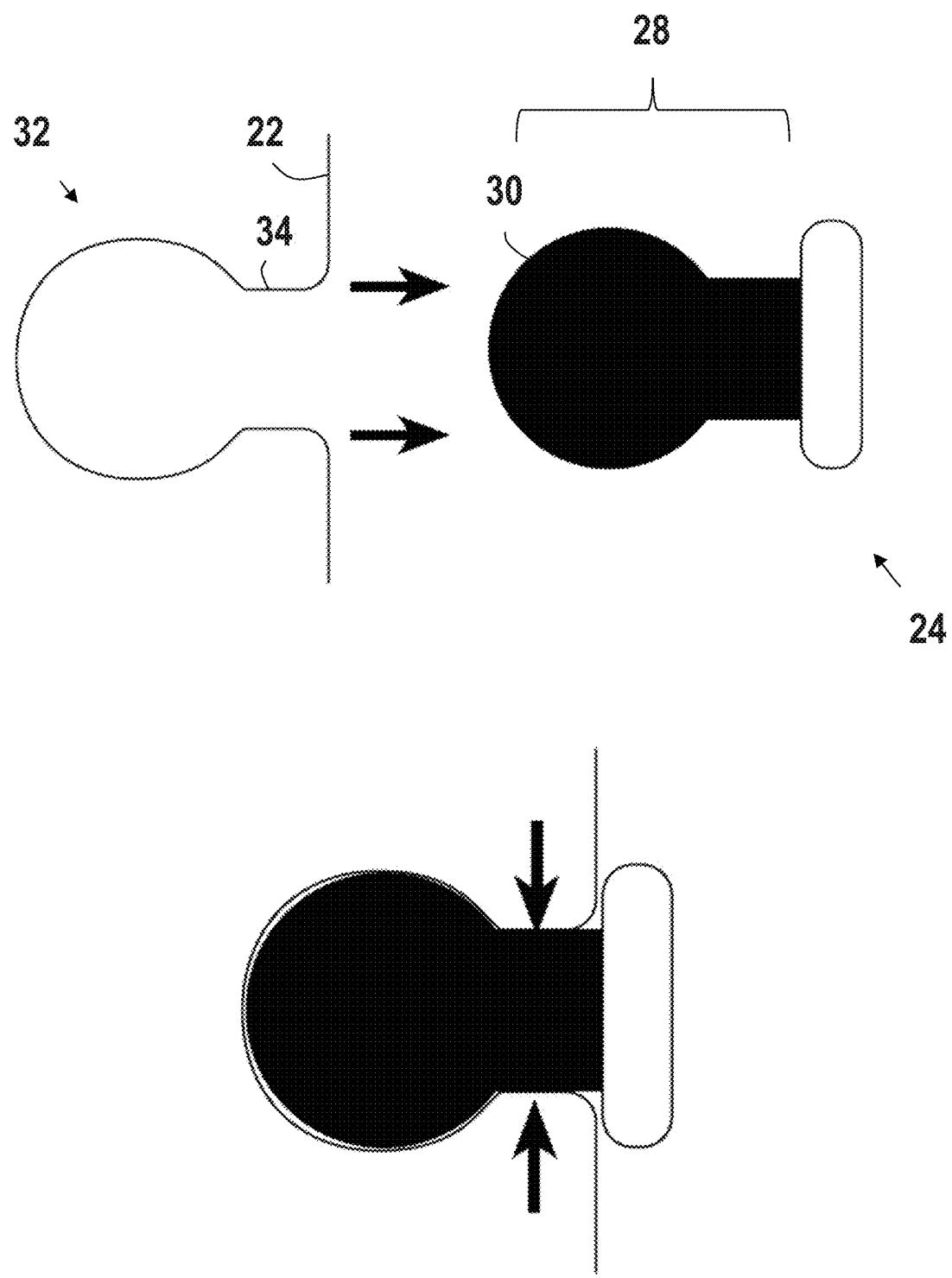
FIG. 7 depicts an exemplary method of engaging the recess 32 of FIG. 3 with a protrusion 28 of an adapter 24.

Moving on to FIGS. 5-7, in another configuration the sidewalls 22 include recesses 32 shaped complementary to the protrusions 28, such as at the bulbous member 30, In such a configuration, the sidewalls 22 can be pressed against the adapters 24 to temporarily bend or stretch a throat 34 of each recess 32 over the bulbous member 30 of the corresponding adapter 24. Continued pushing permits the bulbous member 30 to traverse the throat 34, which once passed, permits the throat 34 to naturally retract to its biased state and firmly grasp the adapter 24 along its outer contour. Removing the sidewall 22 from the adapter 24 includes pulling the sidewall 22 outward, which again bends or stretches the throat 34 to permit removal from the adapter 24. It has been found that by sizing the recess 32 complementary to the bulbous member 30, on the one hand, the face shield 12 is easily pressed over the bulbous member 30 to engage the adapter 24, and on the other hand the bulbous member 30 successfully prevents inadvertent release of the sidewall 22 by the adapter 24.

Figure 8:
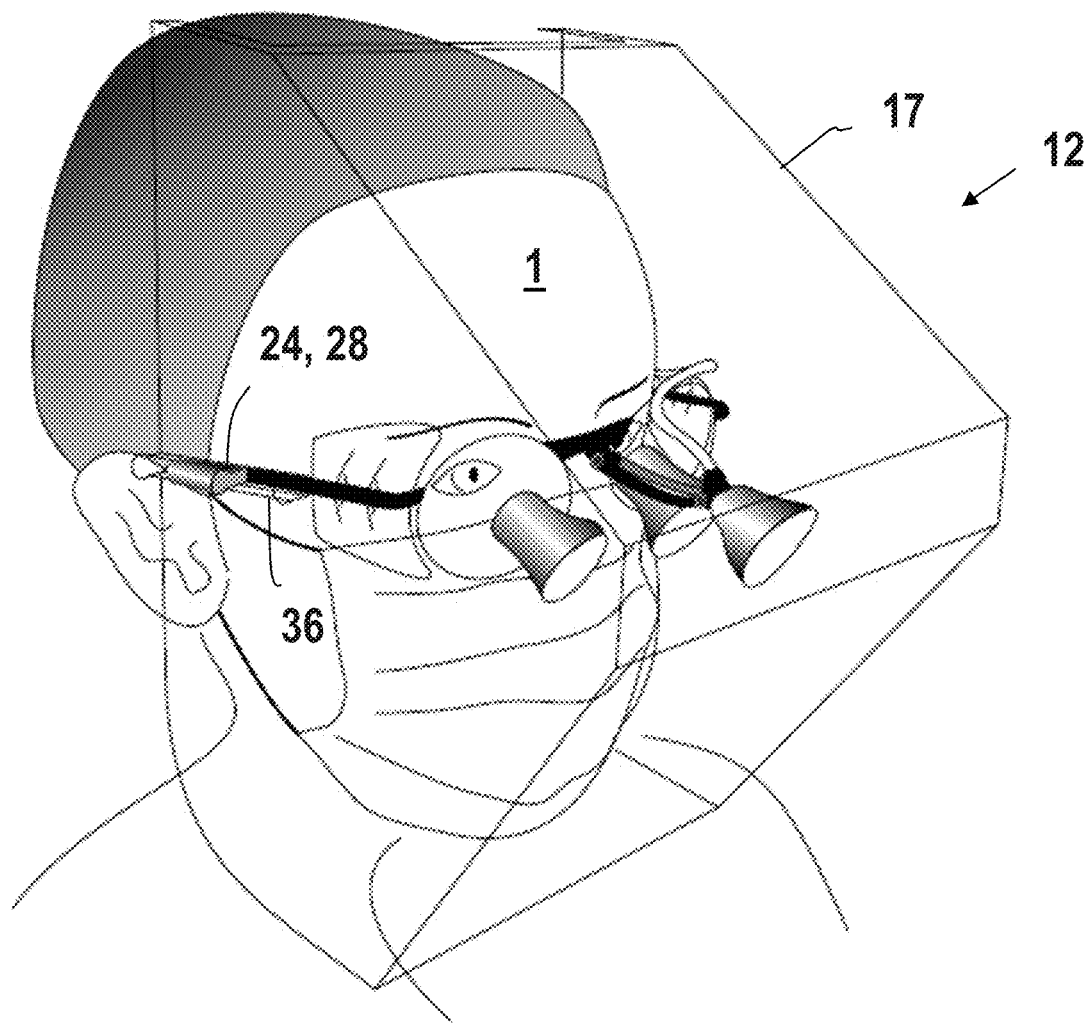
FIG. 8 is a right, top, and front isometric view of an individual wearing another exemplary face shield 12 with recess 36.
Figure 9:
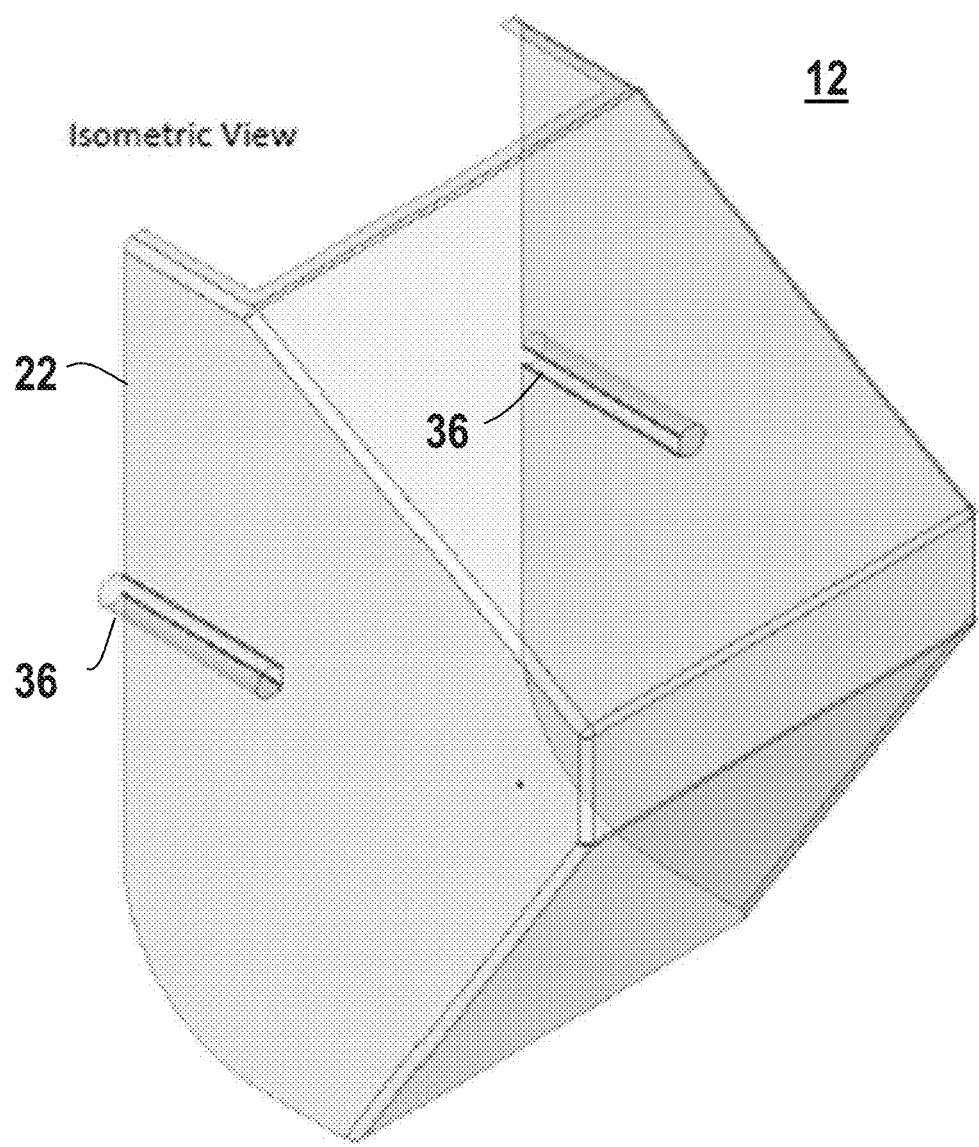
FIG. 9 is a right, top, and front isometric view of the face shield 12 of FIG. 8 with recess 36.
Figure 10:
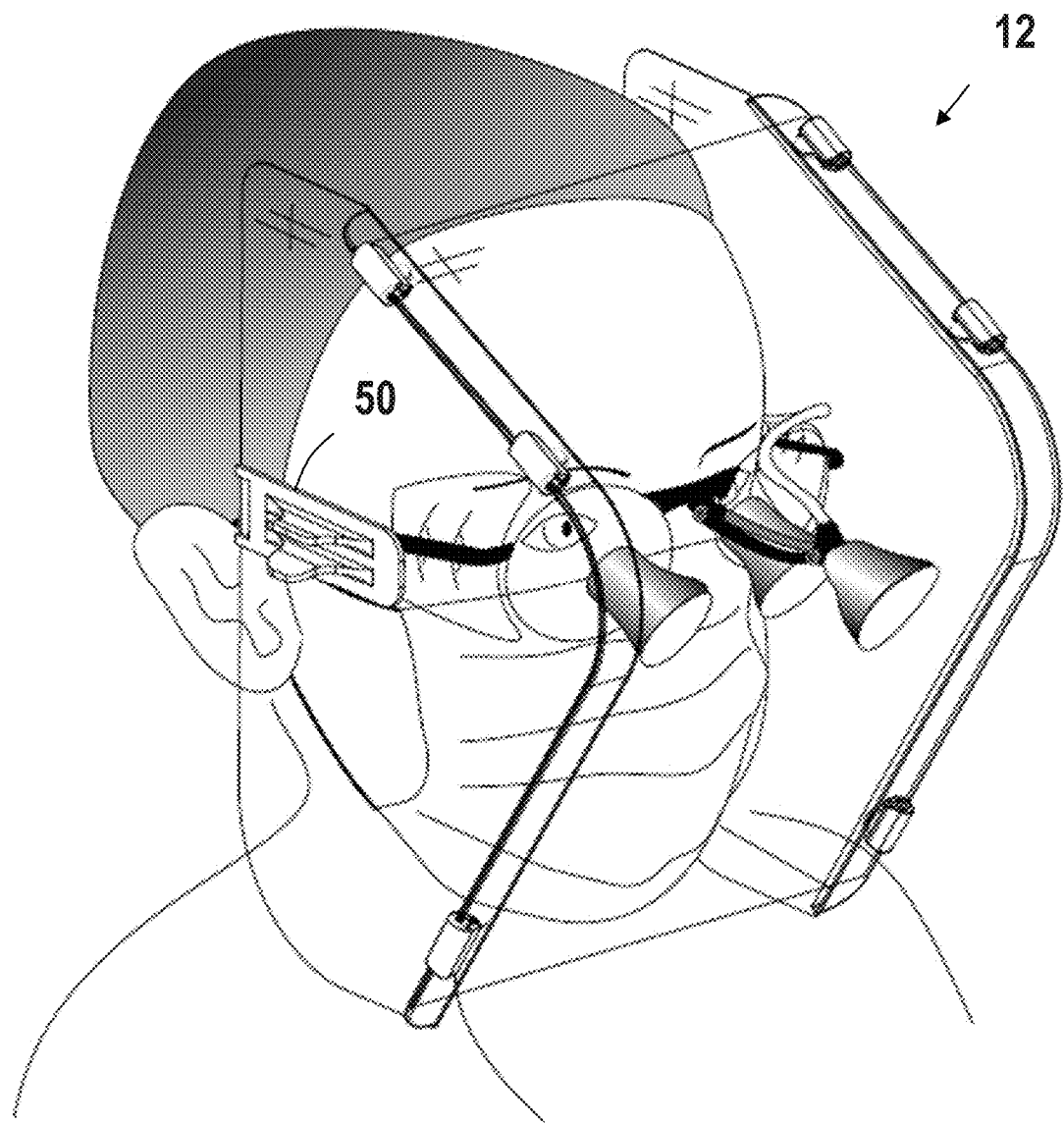
FIG. 10 is a right, top, and front isometric view of an individual wearing still another exemplary face shield 12 with pronged clips 50.
Figure 11:
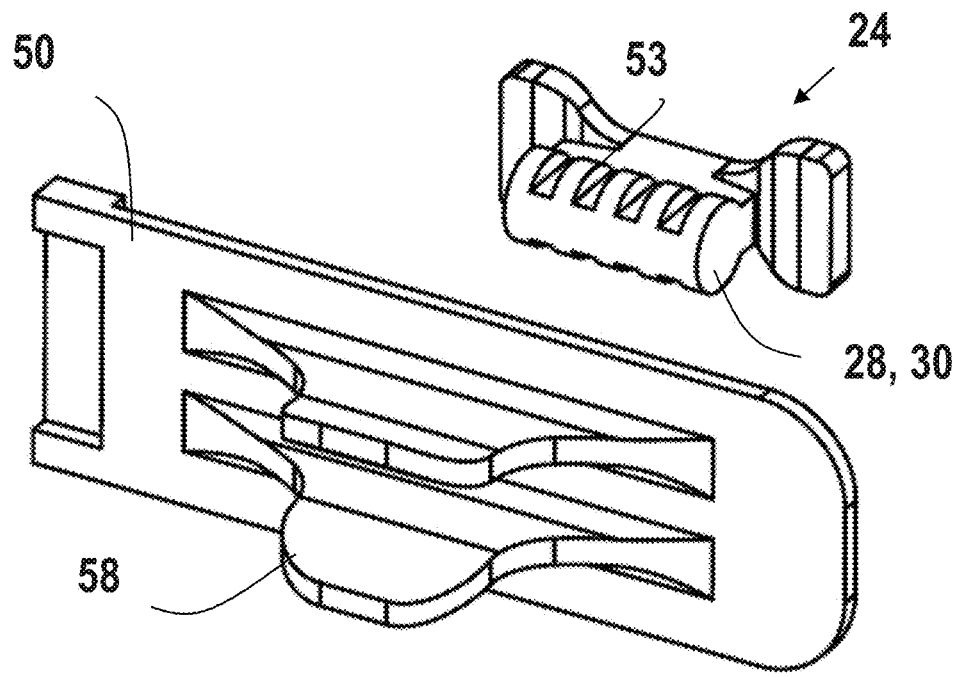
FIG. 11 depicts exemplary adapters 24 paired with pronged clips 50.
Figure 11:
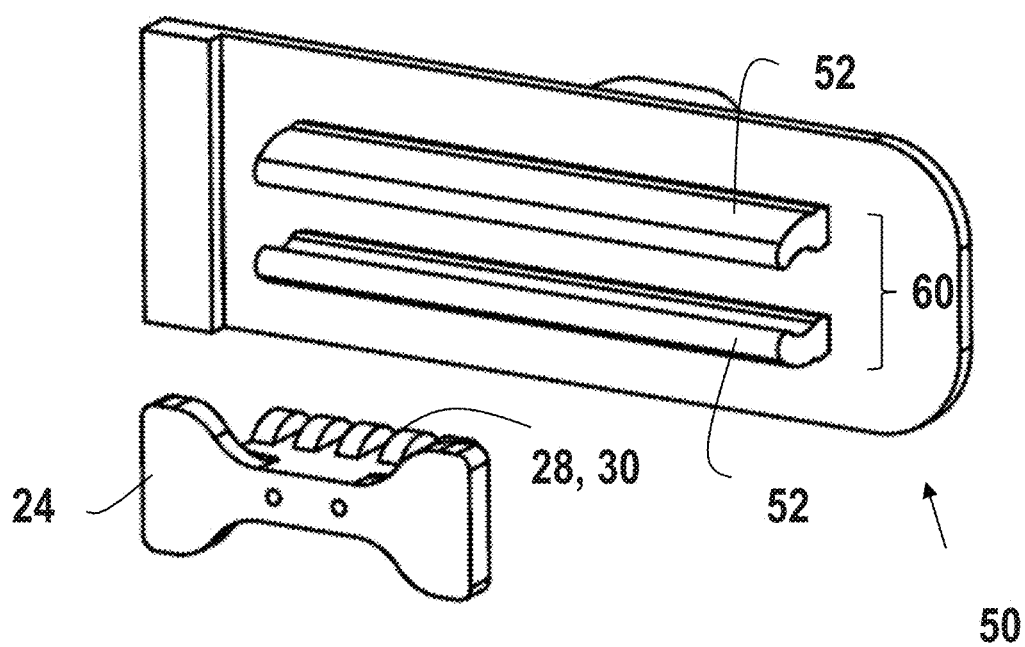
Figure 12:
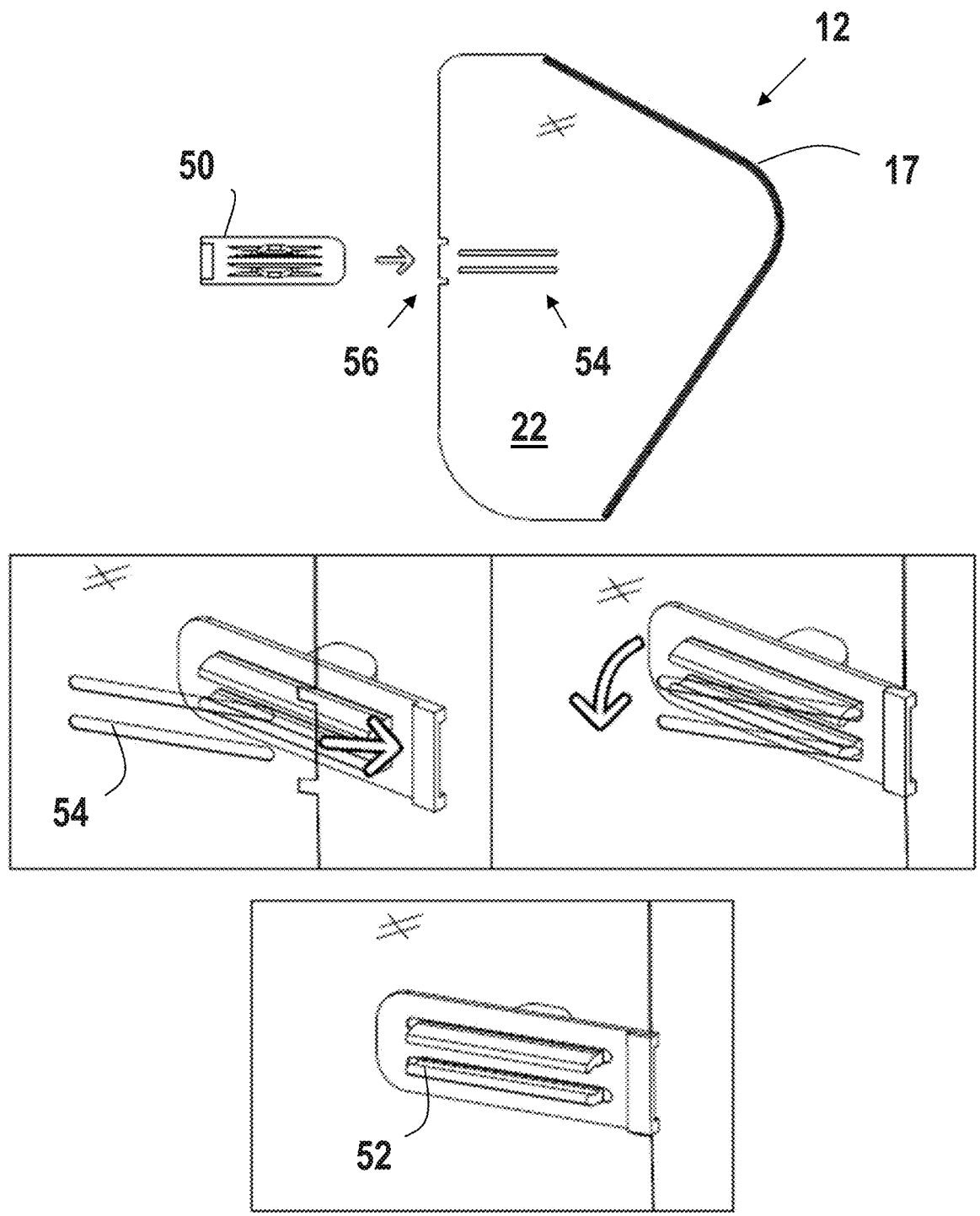
FIG. 12 depicts an exemplary method of assembling pronged clips 50 to a face shield 12.
Figure 13:
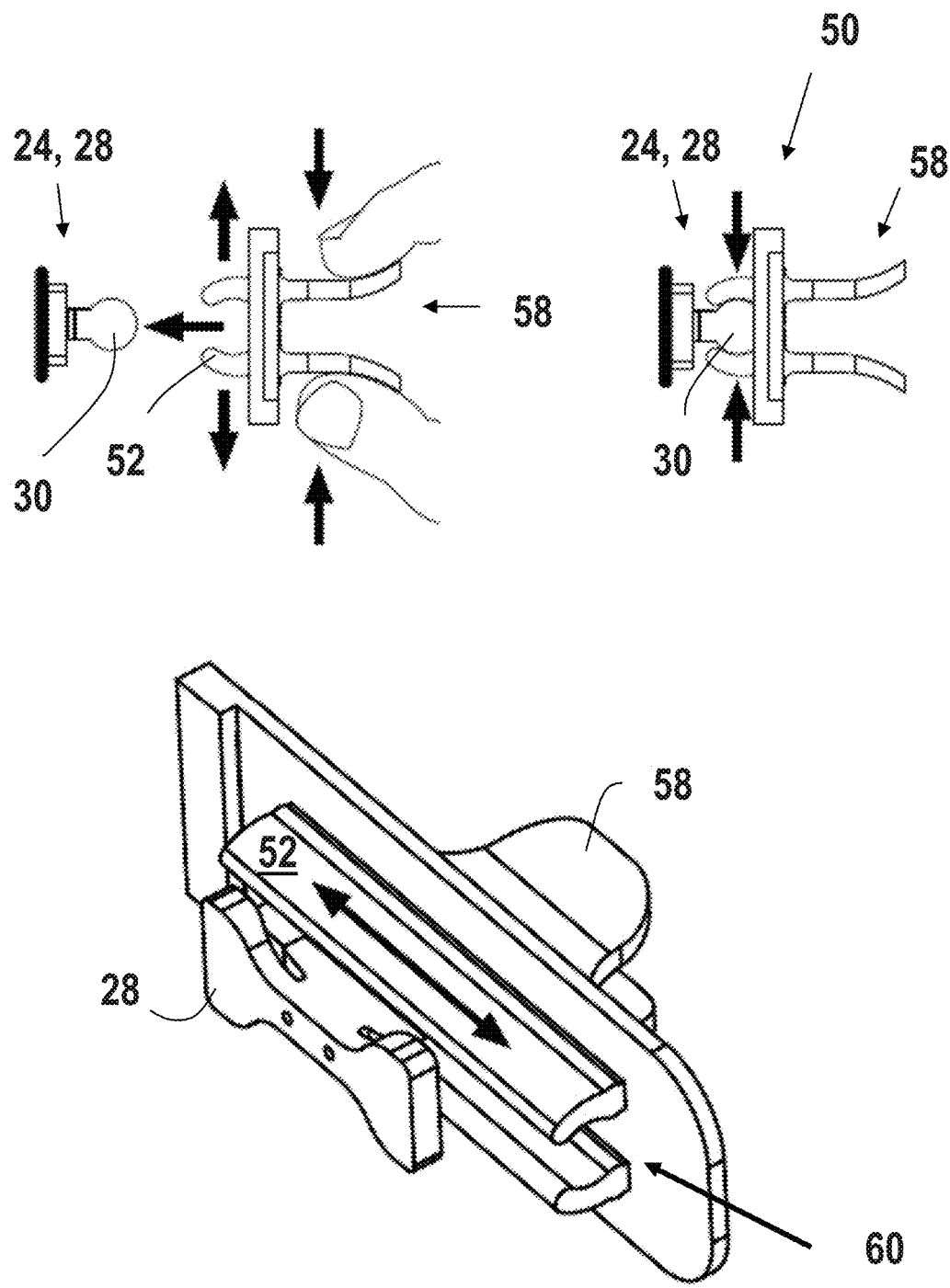
FIG. 13 depicts the grasping or engagement of the adapter 24 with the pronged clip 50 and its adjustment along a track 60.

In a variation of the above, FIGS. 8-9 depict an embodiment with a recessed track 36 shaped complementary to the protrusion 28, such as at the bulbous member 30. By extending the recessed track 32 along each sidewall 22, the face shield 12 can be adjusted inward or outward for improved fitting by sliding the adapter 24 proximally or distally along the track 36. That is, the adapter 24 is slid towards or away from the front 17 of the face shield 12. The face shield 12 is held in place under normal force and thus sliding is prevented in preferred embodiments by the frictional force between the recessed track 36 and adapter 24. The artisan will appreciate that the friction coefficient may be adjusted to balance the force needed for keeping the face shield 12 in place with the force needed for adjustment. In particular, the friction coefficient can be adjusted by adjusting the gap between the complementary-shaped track 36 and the adapter 24, where a larger gap would generally decrease the force needed to slide the adapter 24 along the track 36 or by substituting one material for another in the manufacturing of either the recessed track 36 or adapter 24. Alternatively, a lubricous film may be applied to the inner contour of the recessed track 36 to decrease the coefficient of friction and thus decrease the additional force needed for sliding the adapter 24 along the recessed track 36. In another related approach, the track 36 includes stops, which act to stop the adapters 24 at predetermined positions.

Still another exemplary configuration is depicted in FIGS. 10-13, where the face shield 12 has pronged clips 50 that extend through the face shield 12 to reversibly grasp the adapters 24. In such embodiments, the prongs 52 are preferably shaped complementary to the protrusion 28, such as generally cup-shaped to engage the bulbous member 30. Shown more clearly in FIG. 12, the sidewall 22 can be slotted 54 to feed the prongs 52 through the face shield 12 and can be notched 56 to further assist attachment of the pronged clips 50 to the face shield 12. Shown best in FIG. 11 and FIG. 13, the pronged clips 50 can be operated by pinching a handle 58 positioned outside of the face shield 12 so that the prongs 52 are temporarily opened for positioning the protrusion 28 into or out of the prongs 52. Then releasing the handle 58 so that the prongs 52 return to their biased position, which can securely hold the protrusion 28. As with embodiments previously described the prongs 52 can be elongated to form a track 60, thereby permitting the relative positioning of the adapters 24 towards or away from the front 17 of the face shield 12, for size adjustment. Thus, in some embodiments, the protrusion 28 is engaged or grasped by the prongs 52, the handle 58 is pinched to permit sliding the track 60 along the adapters 24 forward or rearward, and the handle 58 released to firmly grasp or engage the protrusion 28. Releasing the protrusion 28 can include pinching the handle 58 to open the prongs 52 and thus for the subsequent removal of the protrusion 28 from the prongs 52.

Figure 14:
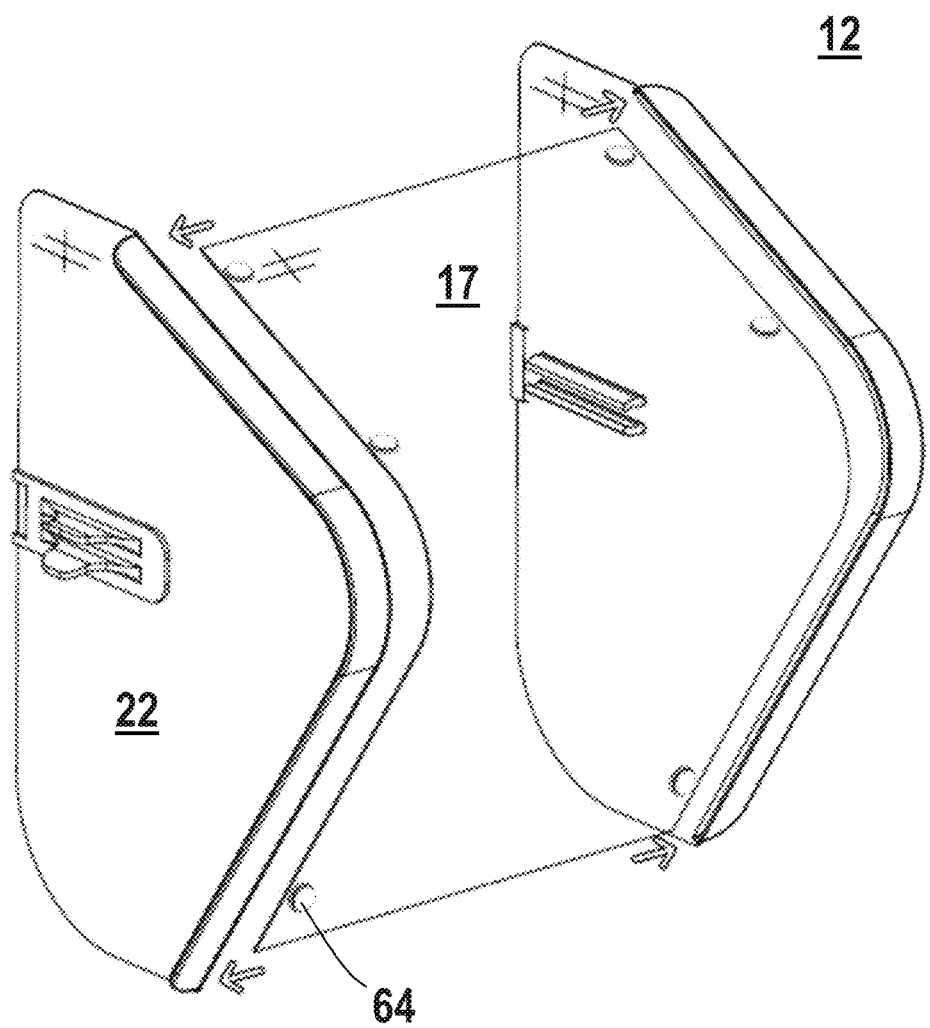
FIGS. 14-15 depict the assembly of a multicomponent face shield 12.
Figure 15:
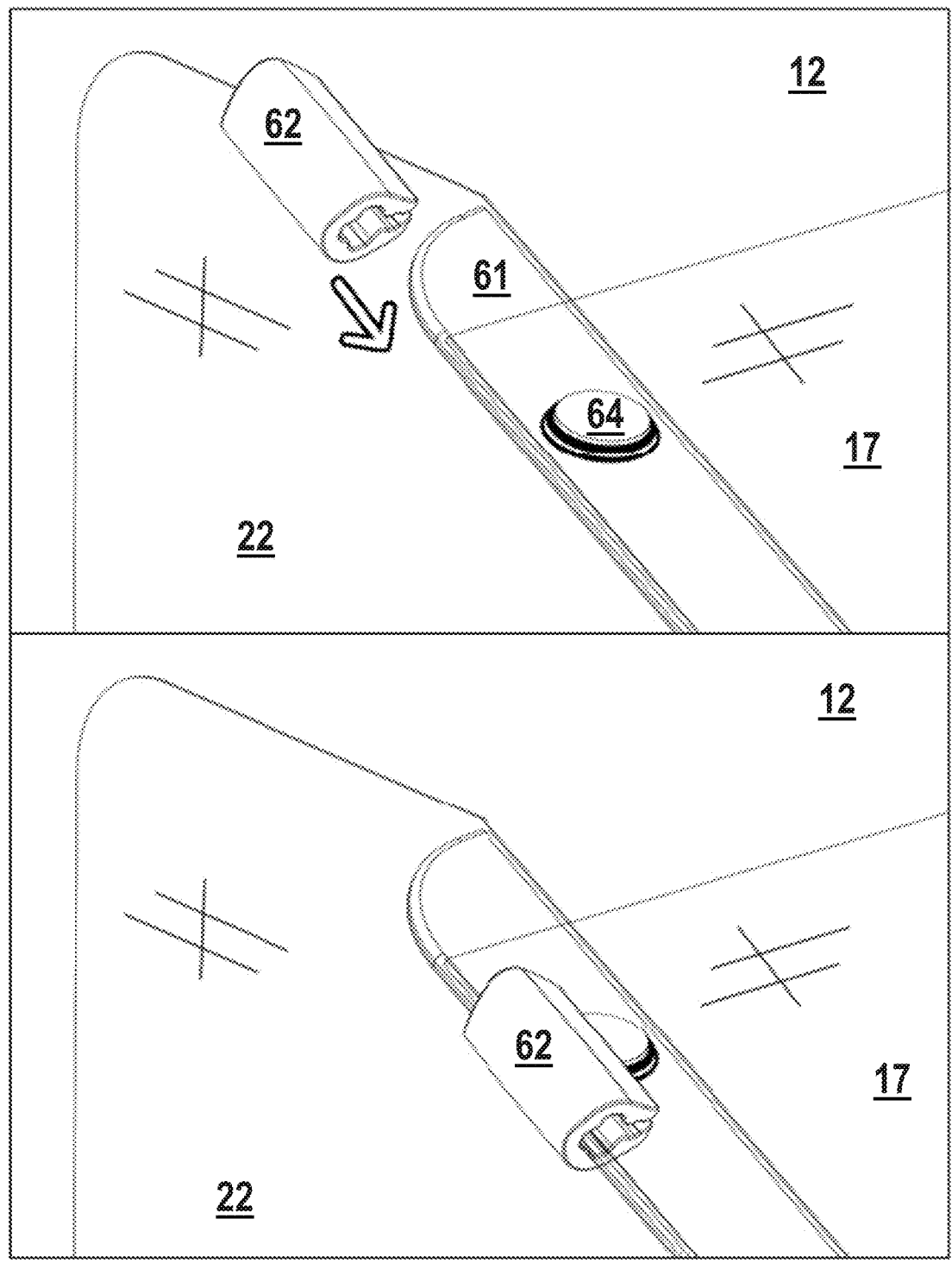

Turning briefly back to the face shield 12. FIGS. 14-15 depict a collapsible configuration, which may be preferred for manufacturing or when shipping the PPE 10 singly. In FIGS. 14-15, the face shield 12 includes raised mounts 64 which are positioned along a lip 61 and firmly gripped by binder clips 64 during assembly. However, in other configurations, the face shield 12 is formed into separate components, then assembled, such as by sliding a front portion 17 into slotted sides 22. In still other embodiments, the front portion 17 can include magnets for magnetic attachment to the lip 61, if metallic, then optionally overlayed with binder clips 62.

Moving on now to the adapters 24, FIGS. 1, 3 and 4 depict an embodiment, where each adapter 24 has two bendable wings 381, 38B (shown best in FIGS. 3-4) extending in substantially a same direction, and the bulbous protrusion 28 extends substantially perpendicular to the longitudinal extent of the two wings 38A, 38B. In such an embodiment, the temple 5 of the eyeglass frame 4 can be clamped between the two wings 38A, 38B (shown best in FIG. 4). Clamping the temple 4 between the wings 38A. 389 can be performed using a variety of mechanisms. For instance, by forming through bores 40 above and below the protrusion 28 along the wings 38A, 389, a line 42 can run through the through bores 40 (preferably also through a through bore 40 of the protrusion 28) and tightened to securely fasten the wings 38A, 388 to the temple 5. In another approach, the wings 38A, 389 having complementary engaging structures, such as snaps or engaging teeth.

Referring more directly to FIGS. 3, 4 and 6, the disclosure also provides a set of adapters 24 for mounting a face shield 12 to a pair of eyeglass frames 4, each adapter 24 having two bendable wings 38A, 388 extending in substantially a same direction and a bulbous protrusion 28 extending substantially perpendicular to the longitudinal extent of the two wings 38A, 38B, where the two wings 38A, 389 have through bores 40 above and below the protrusion 28 and the protrusion 28 has at least one through bore 40. In further embodiments, a means for clamping the adapters to the pair of eyeglasses is provided, such as a line 42 sized for passing through the bores.

Figure 16A:
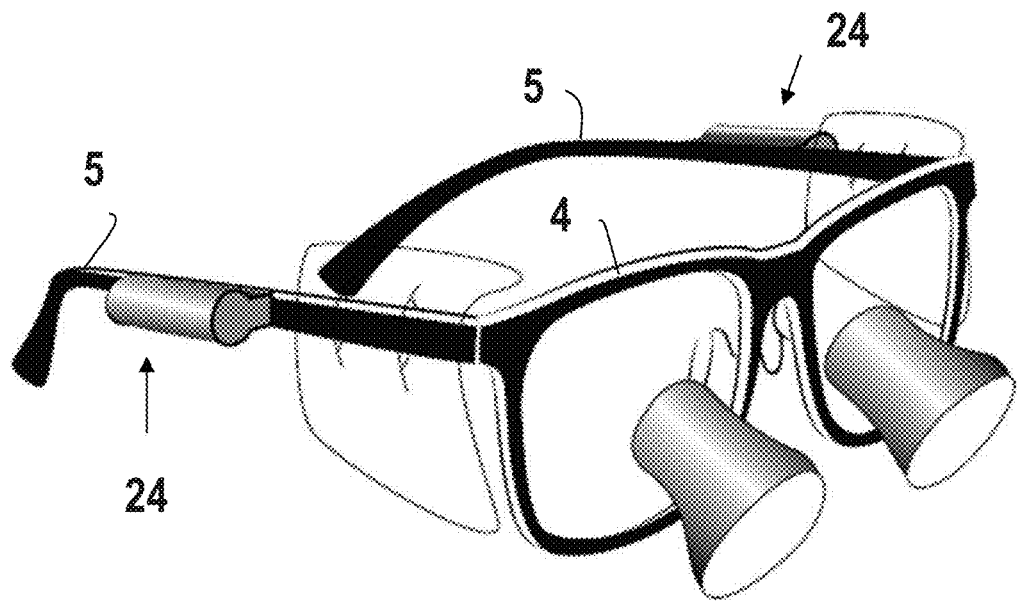
FIG. 16A is a right, top, and front isometric view of a pair of eyeglass frames 4 with an integral adapter 24 extending outward and perpendicular to the longitudinal extent of the temple 5.
Figure 16B:
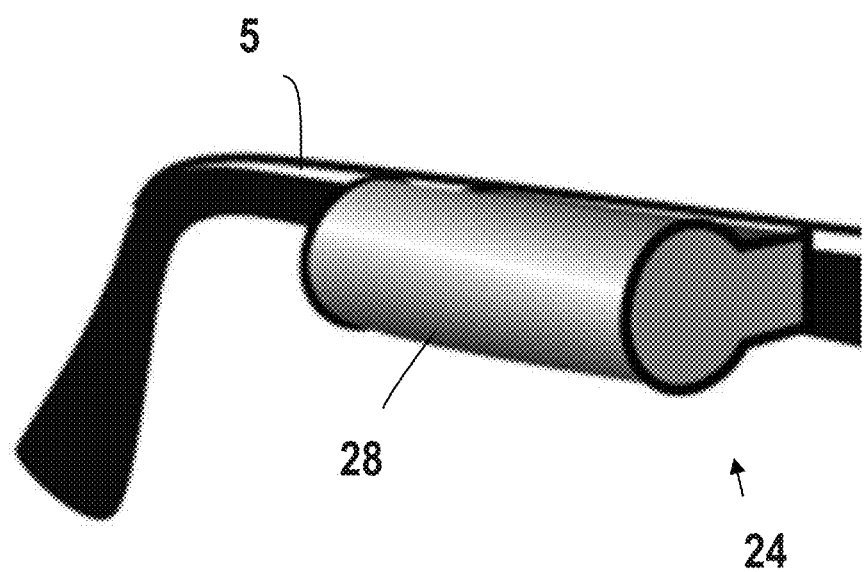
FIG. 16B is an enlarged right, top, and front isometric view showing the bulbous protrusion 28 of the adapter 24 of FIG. 16A integral with the temple 5.

FIGS. 16A-16B provide an embodiment where the adapter 24 is integral to the eyeglass frame 4. In particular, FIG. 16A depicts a pair of eyeglasses having a frame 4 and a pair of longitudinally extending temples 5. The adapters 24 are fused or glued to the temples 5. FIG. 168 more clearly shows each temple 5 having a bulbous protrusion 28 extending outward and perpendicular to its longitudinal extent.

Figure 17A:
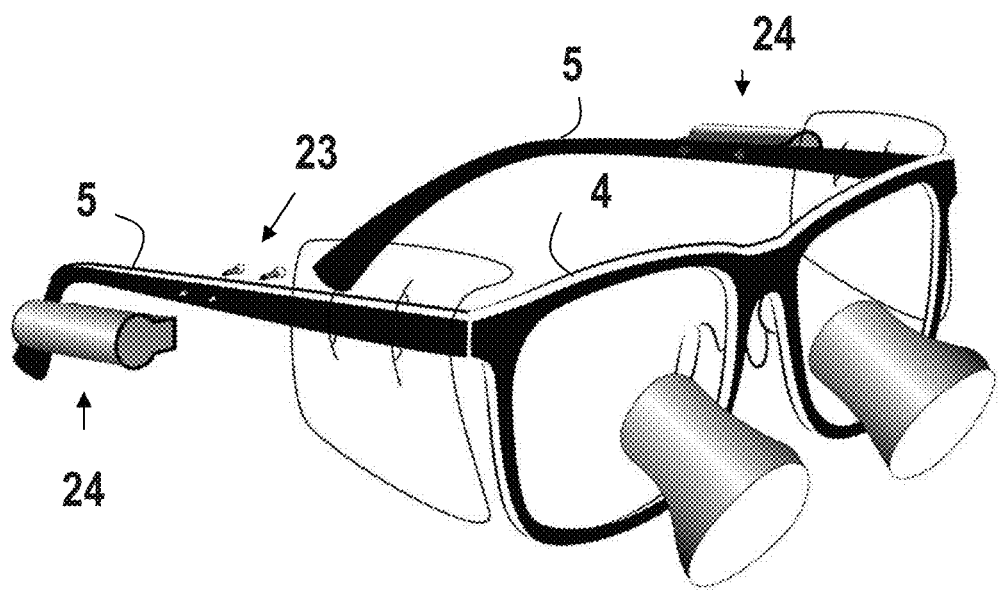
FIG. 17A is a right, top, and front isometric view of a pair of eyeglass frames 4 depicting a bolting mechanism 23 for attaching an adapter 24 to the temple 5.
Figure 17B:
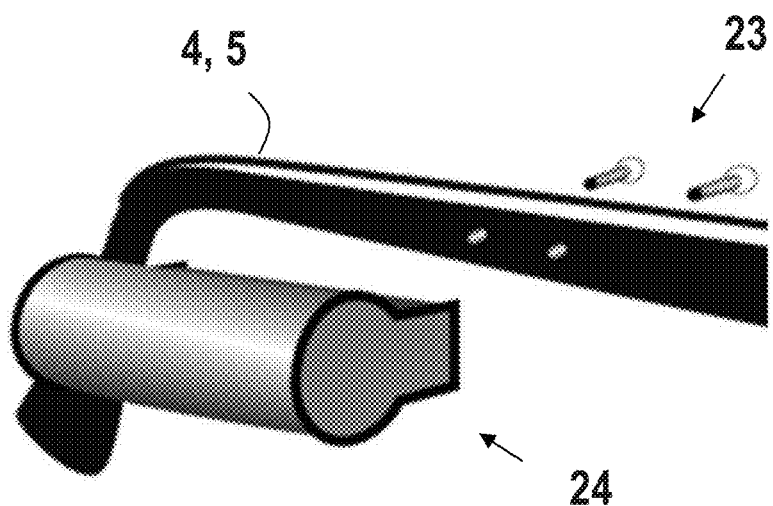
FIG. 17B is an enlarged right, top, and front isometric view showing an exemplary method of attaching the adapter 24 to the temple 5 of eyeglass frames 4 of FIG. 17A.

FIGS. 17A-17B provide an embodiment where adapters 24 are provided for attachment to a set of eyeglass frames 5. In particular, FIG. 17A depicts an adapter 24 configured for attachment to the temples 5 of an eyeglass frame 4 using screws as a bolting mechanism 23. FIG. 17B more clearly shows each adapter 24 can be provided separate from the frame 4 then secured to the temple 5 afterwards.

Figure 18:
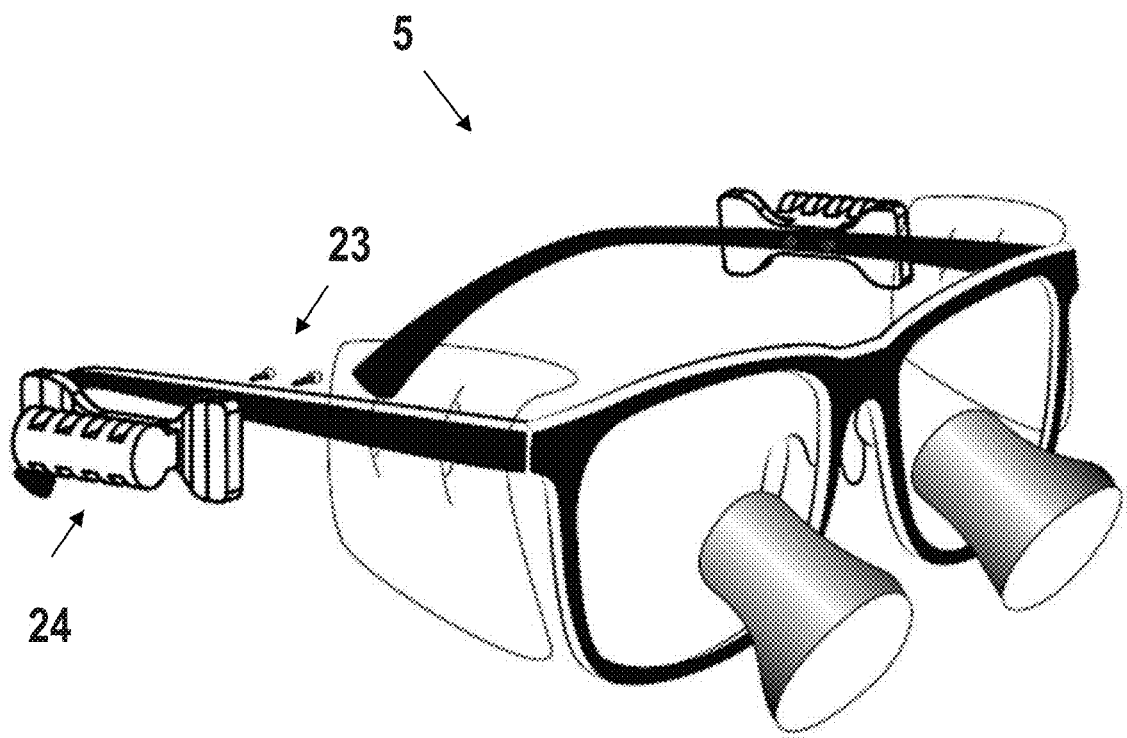
FIG. 18 is a right, top, and front isometric view of another pair of eyeglass frames 4 depicting the attaching of another adapter 24 to the temple 5 using a bolting mechanism 23.
Figure 19:
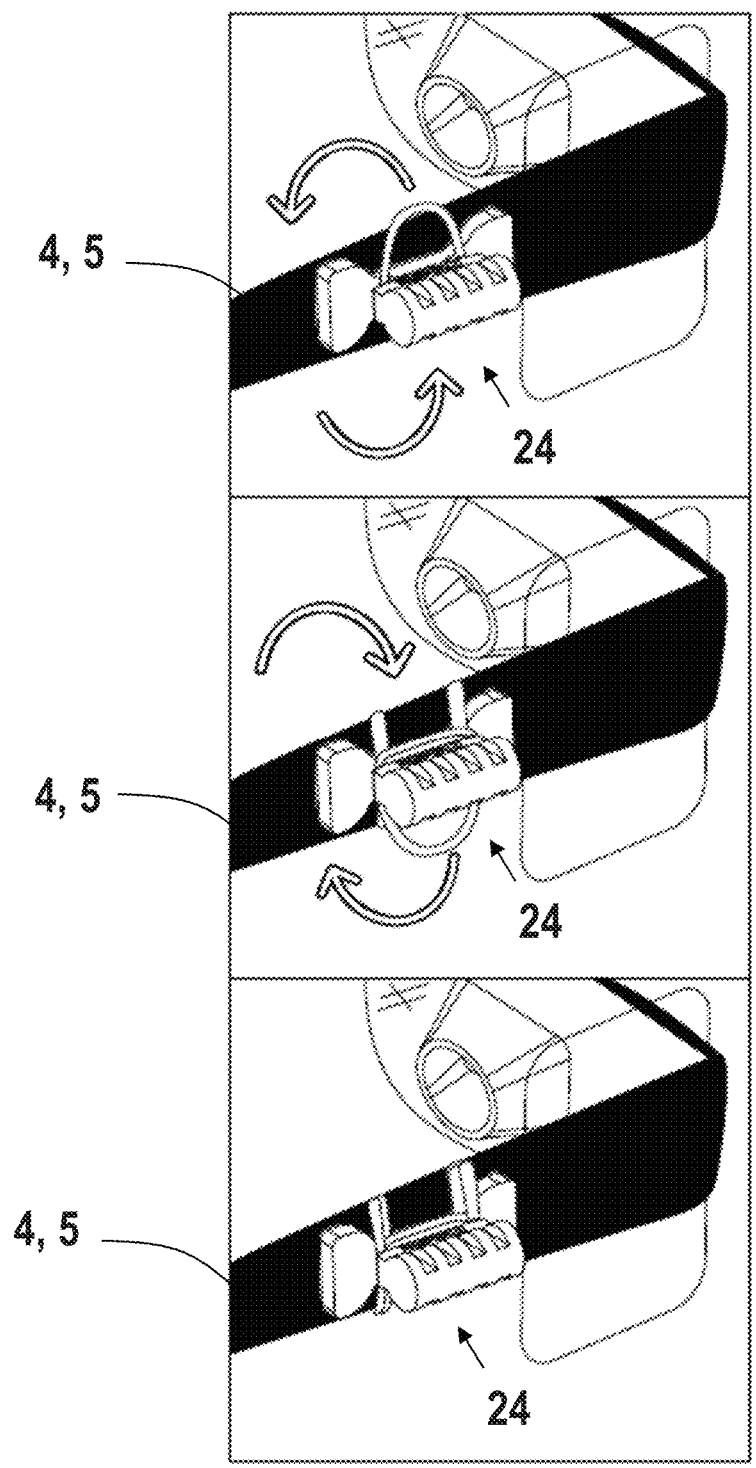
FIG. 19 depicts the tying of an adapter 24 to the temple 5.

FIGS. 18-19 show a hybrid approach where a same adapter 24 is configured for attachment to eyeglass frames 4 using different approaches. In particular, FIG. 18 shows an approach where the adapter 24 is attached to the temple 5 using screws as a bolting mechanism 23 and FIG. 19 shows an approach where the adapter 24 is tied to the eyeglass frame 4.

While the PPE 10 has be described as a whole, its subcomponents also provide an improvement over the att. In particular, referring to FIGS. 1-19 collectively, also disclosed is an eyeglass frame 4, which includes a pair of longitudinally extending temples 5, each temple having a bulbous protrusion 28 extending outward and perpendicular to the longitudinal extent of the temple 5. In some embodiments, the protrusions 28 are integral with the temples 5.

In another related aspect of the invention, a set of adapters 24 for mounting a face shield 12 to an eyeglass frame 4 is provided, each adapter 24 having two bendable wings 38A, 38B extending in substantially a same direction and a bulbous protrusion 28 extending substantially perpendicular to the longitudinal extent of the two wings 38A, 38B, where the two wings 38A, 38B have through bores 40 above and below the protrusion 28, and the protrusion 28 has at least one through bore 40. In some embodiments, a means for clamping the adapters 24 to the eyeglass frame 4 is provided, such as a line 42 sized for passing through the through bores.

The invention described herein may be embodied in other specific forms without departing from the spirit or essential characteristics thereof. The specific embodiments previously described are therefore to be considered as illustrative of, and not limiting, the scope of the invention.

What is claimed is:

1. An article of personal protective equipment (PPE) for covering a wearer's face, the article comprising a set of adapters, each adapter comprising an outward extending protrusion that is mounted or configured for mounting to a temple of an eyeglass frame; and a face shield comprising pronged clips that extend through the face shield to reversibly grasp the set of adapters, wherein the pronged clips are actuated outside of the face shield.

2. The article of personal protective equipment (PPE) of claim 1, wherein the pronged clips each comprise a pinchable handle that opens a pair of prongs when pinched.

3. The article of personal protective equipment (PPE) of claim 1, wherein the pronged clips are elongated to form an adjustable track for adjustably positioning the set of adapters towards and away from a front of the face shield.

4. The article of personal protective equipment (PPE) of claim 1, wherein the face shield comprises opposing sidewalls joined by a convex front with upper and lower portions angled inward to cover a wearer's face.

* * * * *